United States Patent
Rindy et al.

(10) Patent No.: US 8,327,892 B2
(45) Date of Patent: Dec. 11, 2012

(54) VAPORIZER FILLER LOCK AND METHOD OF FILLING A VAPORIZER

(75) Inventors: Ryan W. Rindy, McFarland, WI (US); Robert Q. Tham, Middleton, WI (US); John R. Pinkert, Madison, WI (US)

(73) Assignee: General Electric Company, Schenectady, NY (US)

( * ) Notice: Subject to any disclaimer, the term of this patent is extended or adjusted under 35 U.S.C. 154(b) by 582 days.

(21) Appl. No.: 12/696,138

(22) Filed: Jan. 29, 2010

(65) Prior Publication Data

US 2011/0186046 A1    Aug. 4, 2011

(51) Int. Cl.
*B65B 1/04* (2006.01)

(52) U.S. Cl. ............... 141/351; 141/2; 141/95; 141/302; 141/346; 141/363; 141/364; 141/366

(58) Field of Classification Search ................. 141/2, 18, 141/94, 95, 98, 301, 302, 346–351, 363–366; 128/203.12–203.14, 203.19
See application file for complete search history.

(56) References Cited

U.S. PATENT DOCUMENTS

| | | | |
|---|---|---|---|
| 5,381,836 A | 1/1995 | Braatz et al. | |
| 5,470,511 A | 11/1995 | Laybourne et al. | |
| 5,617,906 A | 4/1997 | Braatz et al. | |
| 5,687,777 A * | 11/1997 | Dobson et al. | 141/18 |
| 5,918,595 A | 7/1999 | Olsson et al. | |
| 6,125,893 A * | 10/2000 | Braatz et al. | 141/18 |
| 6,216,690 B1 * | 4/2001 | Keitel et al. | 128/203.12 |
| 6,585,016 B1 * | 7/2003 | Falligant et al. | 141/352 |
| 6,672,306 B2 * | 1/2004 | Loser et al. | 128/203.12 |
| 6,817,390 B2 | 11/2004 | Falligant et al. | |
| 6,929,041 B2 | 8/2005 | Falligant et al. | |
| 7,418,964 B2 * | 9/2008 | Bottom | 128/203.15 |
| 7,886,783 B2 * | 2/2011 | Rindy et al. | 141/351 |

* cited by examiner

*Primary Examiner* — Timothy L Maust
(74) *Attorney, Agent, or Firm* — Andrus, Sceales, Starke & Sawall, LLP

(57) ABSTRACT

A vaporizer filling system includes a filler assembly, a sump, and a valve. The valve controls fluid communication into the sump. A retaining device retains the valve in an open position. A delay is connected to the retaining device. The delay controls the operation of the retaining device in order to retain the valve in the open position until the delay detects a release condition. The delay then controls the retaining device to release the valve. A method of filling a vaporizer includes engaging a bottle of liquid anesthetic agent with a filler assembly. The bottle and the filler assembly are moved from a first position to a second position. The bottle and filling assembly are locked in the second position with a retaining device. Then the retaining device is released and the bottle and filler assembly are returned to the first position.

20 Claims, 4 Drawing Sheets

VAPORIZER FILLER LOCK AND METHOD OF FILLING A VAPORIZER

BACKGROUND

The present disclosure is related to the field of anesthetic vaporizers. More specifically, the present disclosure is related to a vaporizer filler lock used to assist in filling an anesthetic vaporizer with liquid anesthetic agent.

Anesthetic vaporizers convert liquid anesthetic agent into a gaseous form for delivery to a patient. The liquid anesthetic agent is provided to the vaporizer in relatively small quantities and stored within a sump until it is needed for delivery to a patient.

If an anesthetic agent is inhaled by a person other than the intended patient, it can produce toxic or intoxicating effects on unsuspecting personnel. Therefore, great caution is taken in order to prevent the leakage of anesthetic agent into the ambient air surrounding the anesthetic vaporizer. Additionally, anesthetic agents can be very costly substances and therefore economically minded care providers do not want to waste any of these agents during the process of filling the anesthetic vaporizer.

Therefore, a series of valves must be operated in order to open the sump of the anesthetic vaporizer to fluid communication with a source of anesthetic agent. These valves are further biased in the closed position such that they must be actively operated in order to maintain the open fluid communication.

BRIEF DISCLOSURE

A vaporizer filling system includes a filler assembly and a valve. The filler assembly is configured to couple with an anesthetic agent source. The valve is movable between a first position wherein the valve is closed and a second position wherein the valve is open. A retaining device retains the valve in the second position. A delay is connected to the retaining device. The delay controls the operation of the retaining device to retain the filler assembly in the second position until the delay detects a release condition. When the delay detects a release condition the delay controls the retaining device to release the valve.

A method of filling a vaporizer includes engaging a bottle of liquid anesthetic agent with the filler assembly when the filler assembly is in a first position. The bottle and the filler assembly are moved from the first position to a second position to move a sump valve of the filler assembly from a closed position to an open position. The bottle and the filler assembly are locked in the second position with a retaining device. A controller is operated to maintain the bottle and the filler assembly in the second position with the retaining device. The retaining device that locks the bottle and the filler assembly in the second position is released. The bottle and the filler assembly are returned to the first position and the sump valve is closed.

A vaporizer filling system includes a filler assembly including a sump valve. The filler assembly is configured to couple with an anesthetic agent source. The filler assembly is movable between a first position wherein the sump valve is closed and a second position wherein the sump valve is open. A retaining device retains the filler assembly in the second position. A delay is connected to the retaining device. The delay controls the operation of the retaining device to retain the filler assembly in a second position until the delay controls the retaining device to release the filler assembly to the first position.

BRIEF DESCRIPTION OF THE DRAWINGS

The drawings illustrate the best mode presently contemplated of carrying out the invention. In the drawings.

DETAILED DISCLOSURE

Figure 1:
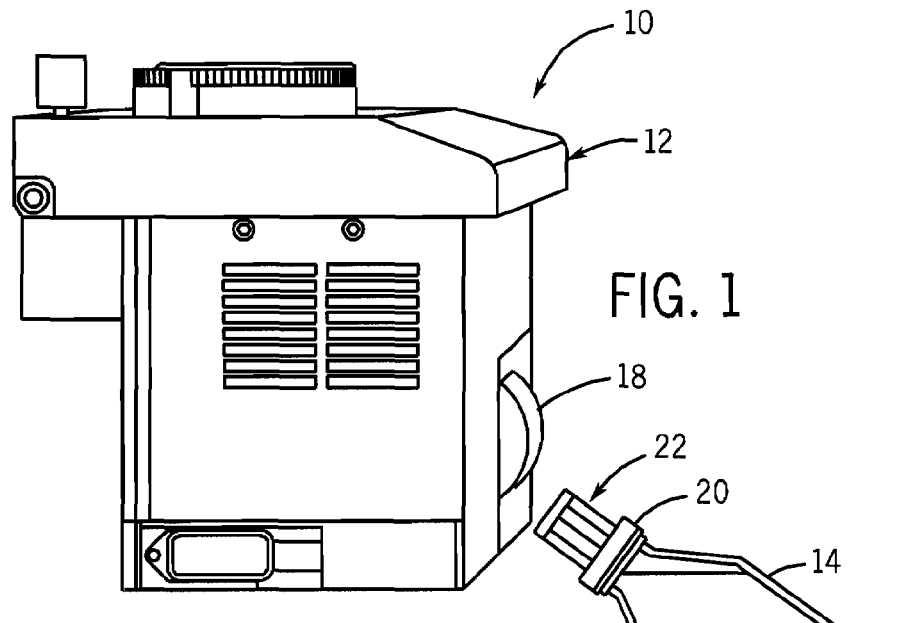
FIG. 1 is depicts an embodiment of a vaporizer filler system.

FIG. 1 depicts a vaporizer system 10. The vaporizer system 10 includes a vaporizer 12 and an anesthetic agent source, which may be a bottle 14 of a liquid anesthetic agent 16.

Presently, many types of anesthetic agents are available for use as the liquid anesthetic agent 16. These anesthetic agents include, but are not limited to: Enflurane (2-chloro-1,1,2-trifluoromethyl), Halothane (1-bromo-1-chloro-2,2,2-trifluoroethane), Isoflurane (1-chloro-2,2,2-trifluoroethyl difluoromethyl ether), Sevoflurane (fluoromethyl 2,2,2-trifluoro-1-(trifluoromethypethyl ether), and Desflurane (2-(difluoromethyoxy)-1,1,1,2-tetrafluoroethane).

Each of these anesthetic agents are typically held in liquid form at room temperature. Therefore, these liquid anesthetic agents 16 may be properly transported in an anesthetic agent source, which may be a vessel such as a bottle 14 for delivery into a vaporizer 12.

Each of the anesthetic agents have different properties and vaporizers are designed to deliver each anesthetic agent differently depending upon the properties of the specific anesthetic agent. Therefore, it is important that the correct type of anesthetic agent is delivered to the vaporizer sump. Various conventions and/or standards, such as those defined by the International Standardization Organization (ISO) help to ensure that the correct anesthetic agent is delivered into a proper sump of the vaporizer. These conventions and standards include the use of various colors to indicate components directed towards the use of specific anesthetic agents. Additionally, the anesthetic bottle and the connection for the anesthetic bottle to the vaporizer are indexed such as through projections, keys, and/or bottle dimensions to ensure that only the proper anesthetic bottle fits the designated vaporizer components designed for that type of anesthetic. This greatly reduces the probability of inadvertently using the wrong type of anesthetic agent within the vaporizer.

Once the liquid anesthetic agent has been delivered to the vaporizer 12, the liquid anesthetic agent is held in a sump (not depicted) and the vaporizer 12 converts the liquid anesthetic agent 16 into a gaseous form such as by heating the liquid anesthetic agent 16 to its boiling point, passing medical gas past the liquid anesthetic agent to saturate the medical gas with anesthetic agent vapor, or by a wicking action to saturate the medical gas with anesthetic agent vapor.

The vaporizer 12 further includes a filler assembly 18 that is designed to engage the bottle 14. The bottle 14 is sealed with a bottle cap 20. The bottle cap 20 includes a bottle valve (not depicted) that maintains the bottle 14 in a normally sealed condition.

The bottle 14 further includes a filler adapter 22 that is configured to engage the filler assembly 18 of the vaporizer 12. The engagement of the filler adapter 22 with the filler assembly 18 establishes a fluid tight seal before the sump valve (not depicted) of the vaporizer 12 and the bottle valve (not depicted) of the bottle 14 are opened, establishing fluid communication between the bottle 14 and the vaporizer 12. This minimizes the loss of the liquid anesthetic agent 16 to the ambient atmosphere around the vaporizer 12 during the transfer of the liquid anesthetic agent 16 from the bottle 14 to the vaporizer 12.

The engagement between the filler assembly 18 and the filler adapter 22 may be one of a variety of engagements such as, but not limited to, a friction fit, a bayonet engagement, a screw engagement, or a latching engagement, that are all considered to be within the scope of the present disclosure.

Figure 2:
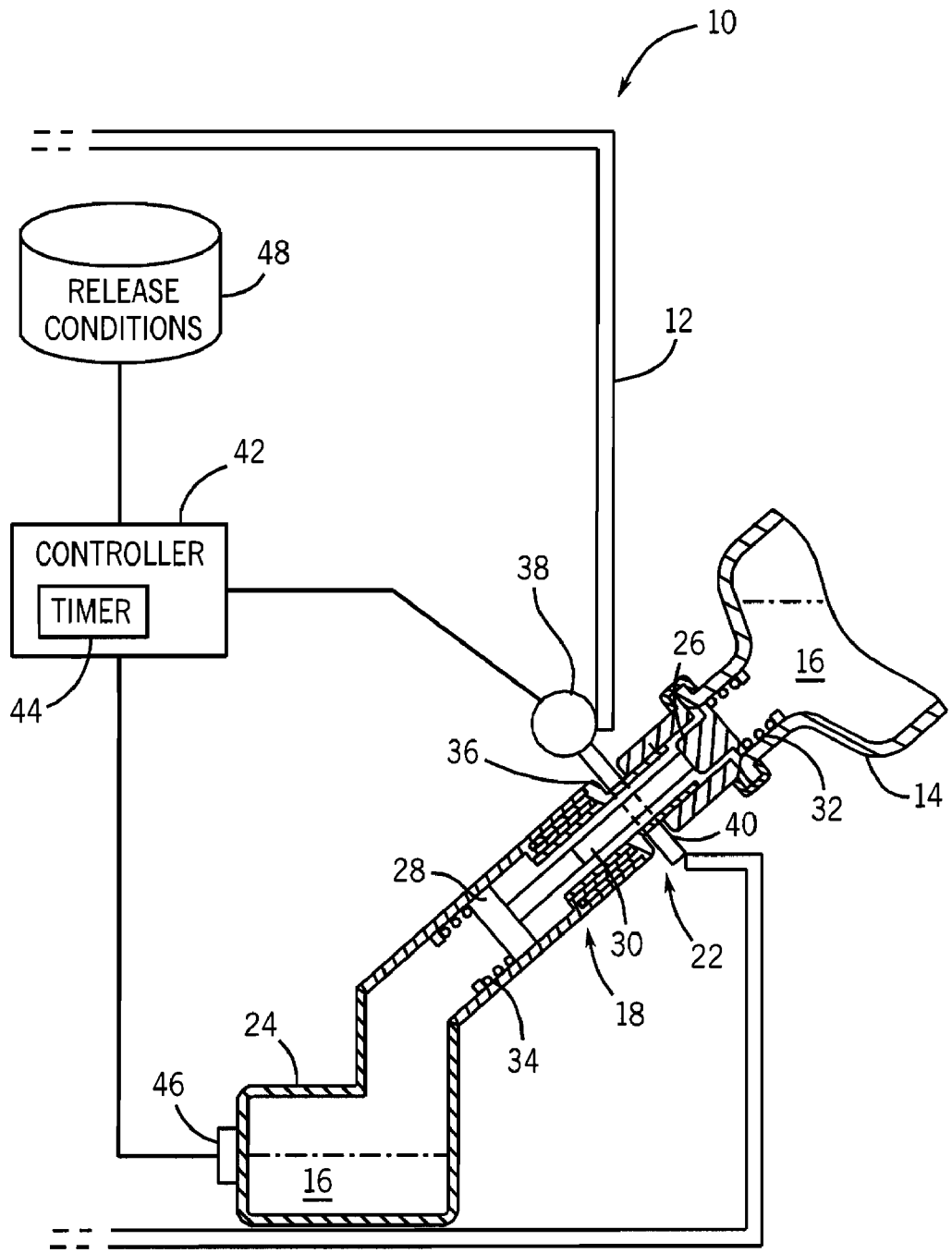
FIG. 2 is a system diagram of an embodiment of the vaporizer filler system.

FIG. 2 is a system diagram depicting the vaporizer system 10 in further operational detail. In this schematic diagram, additional components of the vaporizer 12 are depicted including the sump 24 which is filled with an amount of liquid anesthetic agent 16. The bottle valve 26 is further depicted in the bottle 14 and the sump valve 28 is shown in the filler assembly 18. It should be noted that in alternative embodiments, the filler assembly 18 may further include an additional valve, the filler valve (not depicted) that further closes the filler assembly 18 from fluid communication outside of the vaporizer 12 when a bottle 14 is not engaged with the filler assembly 18.

FIG. 2 depicts a push style vaporizer filling system embodiment wherein once the filler adapter 22 engages the filler assembly 18, the bottle 14 must be pushed into the vaporizer 12 in order to move the bottle 14 and the filler assembly 18 into a filling position. In the filling position, the bottle valve 26 and the sump valve 28 are open to fluid communication of the liquid anesthetic agent 16 from the bottle 14 into the sump 24.

By pushing the bottle 14 into the vaporizer 12, a plunger 30 of the bottle valve 26 engages the sump valve 28. The force placed on the bottle 14 is translated to a bottle valve biasing device 32 and a sump valve biasing device 34. In an embodiment, the biasing devices 32, 34 may be springs or other deformable structures such as to bias the bottle valve 26 and the sump valve 28, respectively, in a normally closed position. By overcoming the biasing forces of the biasing devices 32, 34, the bottle valve 26 and the sump valve 28 are moved to their respective opened positions.

The filler adapter 22 further includes a lip 36. A retaining device 38 of the vaporizer 12 engages the bottle 14 once the bottle 14 is moved to the filling position, which in the embodiment of FIG. 2 is the position wherein the bottle 14 is pushed into the vaporizer 12. In the embodiment depicted, the retaining device 38 includes a latch 40 that engages the lip 36, holding the bottle 14 in this position. While in this embodiment, the retaining device 38 includes a latch 40 that engages a lip 36 of the bottle 14, a wide variety of retaining devices 38 may be used as would be recognized by one of skill in the art. The retaining device 38 may alternatively include a pin, a clip, an interference fit, a collet, a ratchet, a spring, hydraulic controls, or an electromagnetic implementation that serves the purpose of retaining the bottle 14 in engagement with the vaporizer 12 in the filling position wherein the bottle valve 26 and the sump valve 28 are open.

The vaporizer 12 further includes a controller 42 that controls the operation of the retaining device 38. The retaining device 38 serves to hold the bottle 14 in the filling position wherein the liquid anesthetic agent 16 may empty from the bottle 14 into the sump 24; however, when the bottle 14 is locked in the filling position, risk of damage to the bottle 14 or the vaporizer 12 is heightened. Inadvertent jarring or force placed on the bottle 14 may break the bottle 14, filling adapter 22, filling assembly 18, or either of the bottle valve 26 or the sump valve 28. Damage to any of these components may result in opening fluid communication of the liquid anesthetic agent 16 between either the sump 24 or the bottle 14 and the ambient air around the vaporizer 12. Therefore, a delay, which may be a controller 42, operates the retaining device 38 such as to minimize the length of time in which the bottle 14 is held in the filling position.

While the delay is depicted in FIG. 2 as being an electronic controller 42, alternatively, the delay may be a mechanical or electro-mechanical device such as a solenoid or a spring that mechanically or electrically operates the retaining device 38 for a predetermined length of time before releasing the bottle 14.

The delay adds the additional function to the vaporizer 12 of hands-free filling. Previously, a clinician would have to manually hold the bottle 14 in the filling position. This ensured that the bottle 14 wasn't left in the filling position where the bottle 14 or the vaporizer 12 could be damaged as described above. However, with the presently disclosed delay, the clinician is able to place the bottle 14 in the filling position and the retaining device 38 will hold the bottle 14 in the filling position, until the retaining device 38 releases the bottle 14. For a clinician that must keep multiple vaporizers filled with anesthetic agent, this additional feature can save time as the vaporizers can be filled in parallel. The clinician can lock the bottles in the filling position without waiting for each bottle to finish filling the vaporizer before moving on to the next bottle/vaporizer. The clinician can then collect all of the bottles when they are released by the respective retaining devices rather than sequentially filling one vaporizer before moving on to the next.

Returning to the embodiment depicted in FIG. 2, the delay as embodied in controller 42 includes a timer 44 and is programmable such that a specific length of time may be counted based upon settings of the vaporizer 12 between the time in which the bottle 14 is first engaged by the retaining device 38 and the time in which the retaining device 38 is operated by the controller 42 to release the bottle 14. Thus, based upon controls of the vaporizer 12, such as the volume of the bottle 14 and the specific type of liquid anesthetic agent 16, which may be entered into the vaporizer 12 by a clinician, the timer 44 may count through a specified calculated time period that is sufficient for the liquid anesthetic agent 16 to move from the bottle 14 into the sump 24.

In a more detailed embodiment, the controller 42 further is connected to a sensor 46 that is associated with the sump 24. The sensor 46 may be a volume sensor or a weight sensor, or any other suitable type of sensor for monitoring the amount of liquid anesthetic agent 16 within the sump 24. The controller 42 thus uses the input from the sensor 46 that is indicative of the amount of liquid anesthetic agent 16 within the sump 24 such that when the sump 24 is full, the controller 42 operates the retaining device 38 to release the bottle 14, closing the bottle valve 26 and the sump valve 28.

The controller 42 may further be connected to a database of release conditions 48. The database of release conditions 48 may include a plurality of release conditions such as, but not limited to, the volume or the weight of the anesthetic agent in the sump 24. Additionally, these release conditions may include value ranges and combinations of release conditions upon which the controller 42 will operate the retaining device 38 to release the bottle 14.

In one such example, the release conditions in the database of release conditions 48 may include a maximum volume of liquid anesthetic agent 16 in the sump 24, a maximum time that the bottle 14 should be held in the filling position, and if the volume of the anesthetic agent 16 in the sump 24 stops changing. Therefore, the controller 42 monitors the volume of the liquid anesthetic agent 16 in the sump 24 with the sensor 46 to determine if either of the volume reaches the maximum sump volume, or if the volume of anesthetic agent 16 in the sump 24 stops changing. These are likely two more common release conditions of the three to be achieved in this embodiment. The first release condition indicates that the sump 24 is full, and the second release condition indicates that the bottle 14 is empty. Additionally, the controller 42 monitors the overall length of time that has elapsed with the bottle 14 in the filling position, as monitored by the timer 44. In the event of a slowly filling sump, whether caused by occlusion of the flow path of the anesthetic agent, or the rapid evaporation of at least some of the anesthetic agent, neither of the first two release conditions may be met in a reasonable time period. Therefore, the timed release condition ensures that the bottle 14 is not held in the filling position for longer than a defined maximum length of time. When the first of any of the release conditions are met, the controller 42 operates the retaining device 38 to release the bottle 14.

In an additional embodiment, a further or alternative sensor (not depicted) is associated with the sump 24. This further sensor measures temperature within the sump 24. The temperature may be used by the controller 42 in order to adjust or calibrate the evaluation of release conditions. As an example, during operation of the vaporizer 12, the sump 24 may be heated to a temperature that is above the boiling point of the liquid anesthetic agent 16 within the sump 24. If additional liquid anesthetic agent 16 is introduced to the sump 24 during the operation of the vaporizer 12, then this increased temperature will convert some of the liquid anesthetic agent 16 directly into anesthetic agent vapor. This will affect the time and volume required to fill the sump to a desired volume. Alternatively, the temperature of the sump 24 may affect the flow rate of the liquid anesthetic agent 16 from the bottle 14 into the sump 24. In order to minimize the length of time that the bottle 14 is held in the filling position, while also achieving desirable filling of the sump 24 with liquid anesthetic agent, the controller 42 can adjust the release conditions to account for these additional factors.

Figure 3:
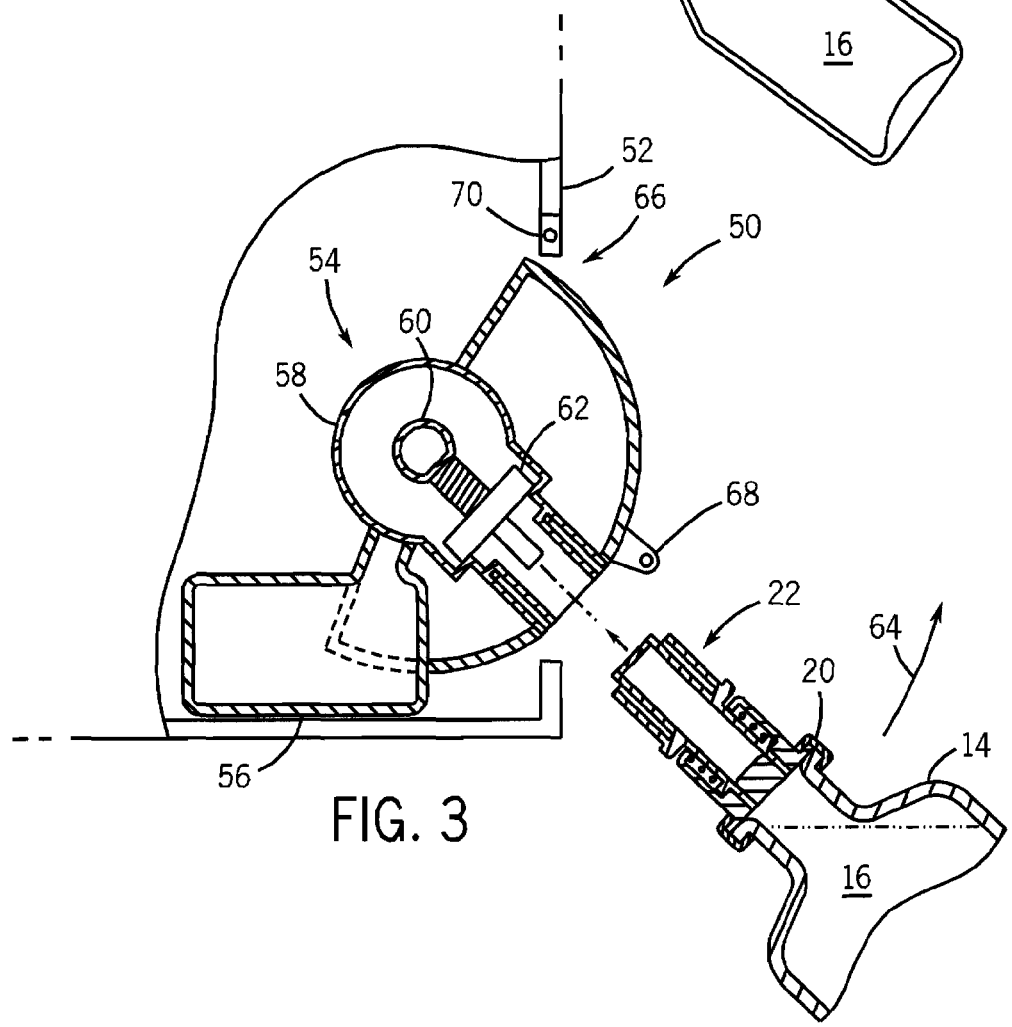
FIG. 3 depicts a rotational embodiment of the vaporizer filler system.

FIG. 3 depicts an alternative embodiment of a vaporizer system 50. The vaporizer system 50 includes a vaporizer 52 with a rotational-style filler assembly 54. The vaporizer 52 further includes a sump 56 that holds liquid anesthetic agent 16. The sump 56 is connected to the filler assembly 54 through a sump valve 58 that operates as a rotational sump valve 58. The sump valve 58 on the filler assembly 54 moves from a closed position to an open position by rotating the filler assembly 54 about a pivot point 60 such that the sump valve 58 slides into alignment with an opening of the sump 56, thereby establishing fluid communication between the filler assembly 54 and the sump 56.

As disclosed previously above, the bottle 14 includes a bottle cap 20, a filler adapter 22, and a bottle valve (not depicted). The filler adapter 22 engages the filler assembly 54 of the vaporizer 52. In the vaporizer 52, the filler assembly 54 further includes a filler valve 62 that is engaged by the filler adapter 22 when the bottle 14 is inserted into the filler assembly 54. The filler valve 62 operates to open and close the filler assembly 54 to fluid communication outside of the vaporizer 52. Thus, the filler valve 62 serves as a precautionary valve to keep the liquid anesthetic agent from leaking out of the sump 56 and into the ambient air around the vaporizer 52. Additionally, the filler valve 62 keeps any residual anesthetic agent within the filler assembly 54 after the filling process from exiting the filler assembly 54 into the ambient air around the vaporizer 52. While the filler valve 62 is depicted as being operable with an inward force from the bottle, other embodiments may operate the filler valve 62 with the rotation of the filler assembly 54 such as with a linkage or a cam.

It should be noted that in an alternative embodiment, the vaporizer 50 of FIG. 3 may be implemented without the rotational sump valve 58. In the embodiment (not depicted) the filler assembly 54 is open to fluid communication with the sump 56 and the filler valve 62 operates as the sump valve, controlling the fluid communication between the bottle 14 and the sump 56. It is, therefore, understood that any valve in the filler assembly 54 that operates to control fluid communication between the filler assembly 54 and the sump 56 is recognized as the sump valve.

Referring back to the vaporizer 50 depicted in FIG. 3, in operation, the filler adapter 22 is inserted into the filler assembly 54. The filler adapter 22 and the filler assembly 54 may engage with a friction fit, a screw fit, or a bayonet connection, or any other suitable type of connection as would be recognized by one of skill in the art.

After the filler adapter 22 is engaged with the filler assembly 54, the bottle 14 is rotated in the direction of arrow 64 about the pivot point 60 until the bottle 14 is in the filling position. The rotation of the bottle 14 also rotates the filler assembly 54 to the filling position such that the sump valve 58 moves from its normally closed position into an open position, opening fluid communication between the filler assembly 54 and the sump 56.

Additionally, the rotation of the bottle 14 in the direction of arrow 64 about the pivot point 60 further mechanically opens the bottle valve (not depicted) such that when the bottle 14 reaches the filling position, fluid communication between the interior of the bottle 14 and the sump 56 is opened and the liquid anesthetic agent 16 can flow from the bottle 14 into the sump 56.

The vaporizer 52 includes an alternative embodiment of the retaining device 66. In this embodiment, a hole 68 on the filler assembly 54 is engaged by a pin 70 of the vaporizer 52. The pin is operated by the delay (not depicted) such as is described above with respect to FIG. 2 in order to retain the bottle 14 in the filling position until a release condition of the delay is met. This embodiment is contrasted from that depicted in FIG. 2 in that the retaining device 66 engages the filler assembly 54, rather than the bottle 14. However, it is to be understood that both configurations, or any others similar as recognized by one of ordinary skill in the art, for the retaining device are suitable within the present disclosure.

When a release condition of the delay is met, the delay operates the retaining device 66 such as to release the pin 70 from the hole 68 of the filler assembly 54. The bottle 14 is then released from the filling position and returned to a resting position. In an embodiment, precautions are taken such that the bottle 14 or the filler assembly 54 are not damaged after the release of the retaining device 66. Therefore, a biasing device (not depicted) may be associated with the bottle 14 or the filler assembly 54 such as to slow or impede the movement of the bottle 14 and the filler assembly 54 from the filling position to the resting position. The biasing device may include, but is not limited to, mechanical resistance, hydraulic, lost motion, or spring biasing. In a still further embodiment, the bottle 14 and the filler assembly 54 may be mechanically driven between the filling position and the resting position.

In alternative embodiments (not depicted), it is further to be understood that the control of the filler assembly and/or valve disposed within the system, including the sump valve, filler valve, and bottle valve may further be controlled such as to control the fluid communication between the bottle and the sump. Such control may reduce or increase the flow rate of the anesthetic agent from the bottle to the sump such as by operating one or more of the valves at a position between a fully closed position or a fully open position. In examples of these embodiments, the retaining device may include one or more intermediate positions between the filling position and the resting position. The retaining device may hold the filler assembly/bottle in a selected one of these intermediate positions such as to increase or decrease the flow of anesthetic agent from the bottle into the sump.

While the vaporizer has been presently disclosed with respect to specific embodiments of coordinated valves, retaining devices, and controls, it is to be understood by one of skill in the art that these embodiments are merely exemplary in nature and that alternative embodiments may be constructed by combining elements and features of disclosed embodiments within the scope of this disclosure. This includes embodiments that combine various sump valves, bottle valves, delays, and retaining devices that are disclosed herein, although not explicitly disclosed together as a specific embodiment.

Figure 4:
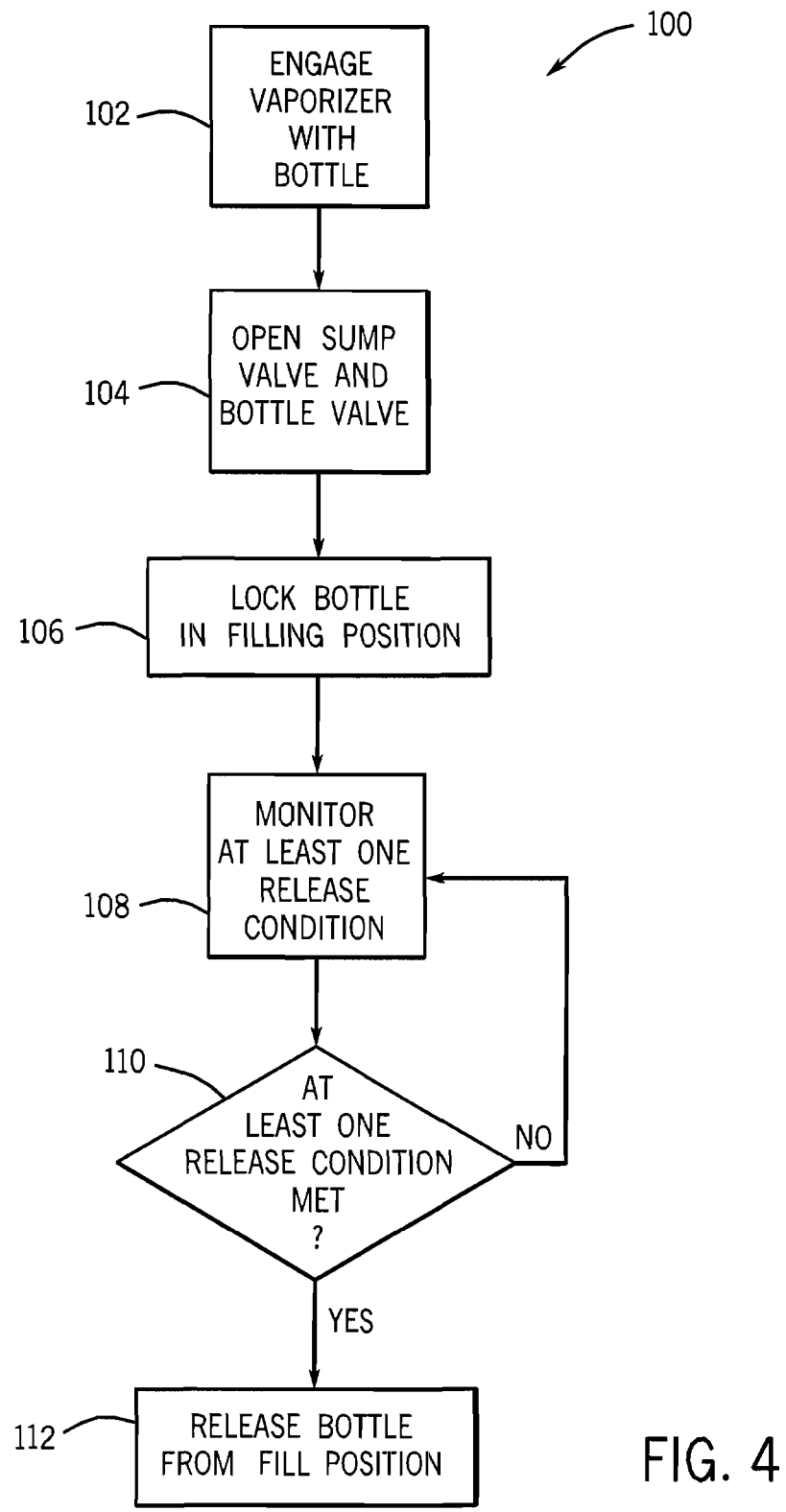
FIG. 4 is a flow chart depicting a method of filling a vaporizer.
Figure 5:
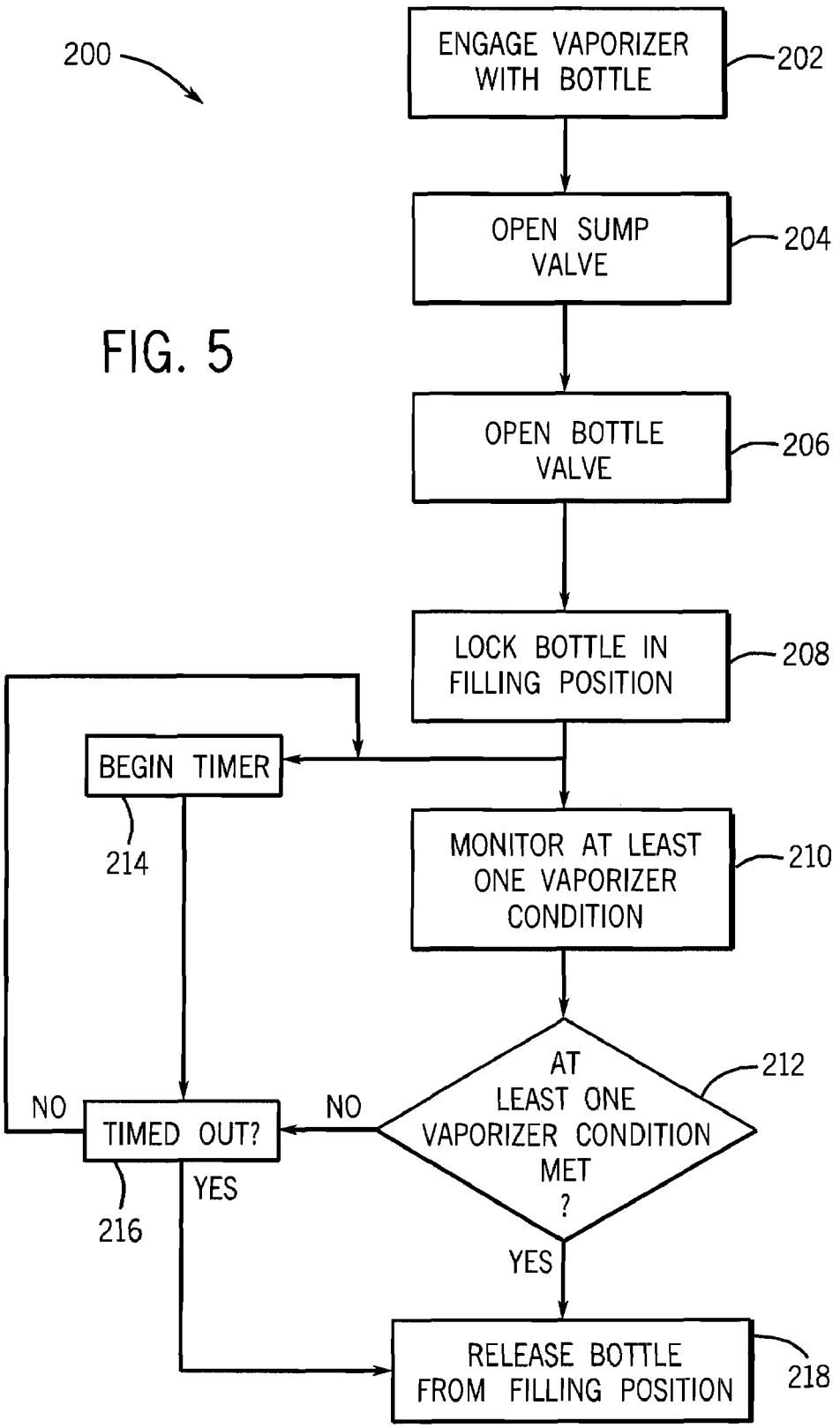
FIG. 5 is a flow chart depicting an alternative embodiment of a method of filling a vaporizer.

FIGS. 4 and 5 are flow charts depicting embodiments of methods of filling a vaporizer with anesthetic agent. FIG. 4 is a flow chart depicting a first embodiment of the method 100. The method begins at 102 by engaging the vaporizer with a bottle of liquid anesthetic agent. As disclosed above, the anesthetic agent may be any of those known anesthetic agents that are stored and/or supplied to a vaporizer in a liquid form. The engagement of the bottle with the vaporizer may also be in any of a variety of ways, including friction fit, screw engagement, or bayonet engagement, but is not intended to be limited to these types of mechanical engagements.

Next, a sump valve on the vaporizer and a bottle valve on the bottle are opened at 104 to establish fluid communication between the bottle and the sump of the vaporizer. By establishing fluid communication between the bottle and the sump, the liquid anesthetic agent inside of the bottle can flow from the bottle into the sump for delivery to the vaporizer.

At 106, the bottle is locked in the filling position. The locking of the bottle in the filling position may be performed by a retaining device. This retaining device may include, but is not limited to, any of a variety of suitable retaining devices, such as pins, clips, ratchets, springs, as well as electromagnetic, interference fit, and hydraulic based retaining devices. The retaining device locks the bottle in the filling position at 106 in order to maintain the bottle in the filling position for a sufficient amount of time in order for the liquid anesthetic agent to flow from the bottle into the sump.

Therefore, at 108, at least one release condition is monitored to determine the proper timing for the release of the bottle from the filling position. The at least one monitored release condition may include a length of time that the bottle is in the filling position or may alternatively include the volume of anesthetic agent in the sump. At 110, it is determined whether or not the at least one release condition has been met. If it is not met, then the at least one release condition is further monitored until at least one release condition is met. When at least one release condition is met at 110, then the retaining device releases the bottle from the filling position at 112. The release of the bottle from the filling position at 112 closes the sump valve and the bottle valve while minimizing risk of leakage of anesthetic agent and potential damage to the vaporizer or the bottle. In embodiments, to further limit the risk of damage to the bottle, the bottle is lowered from the filling position to a resting position where the bottle is supported until it can be gathered by a clinician.

FIG. 5 is a flow chart depicting an alternative embodiment of the method of filling a vaporizer 200. The method 200 begins similarly to the method 100 depicted in FIG. 4 by engaging the vaporizer with a bottle at 202. The sump valve of the vaporizer is opened at 204 and the bottle valve of the bottle is opened at 206. While the sump valve and the bottle valve may be opened in any order, the opening of one or more of the sump valve and the bottle valve is achieved by moving the bottle from a resting position to a filling position. This movement of the bottle may be rotational movement about a fixed point on the vaporizer or the movement could alternatively be pushing the bottle in toward the vaporizer. Alternative types of bottle movement including, but not limited to, screw and latching movements may further be contemplated in other embodiments.

Next, at 208, the bottle is locked in the filling position. Once the bottle is moved into the filling position, it may be automatedly locked using a retaining device of any of the embodiments as disclosed herein such as to lock the bottle in the filling position.

Once the bottle is locked in the filling position at 208 two types of monitoring are performed. At 210, at least one vaporizer condition is monitored. The vaporizer condition may be, but is not limited to, a maximum volume of liquid anesthetic agent in the sump. Alternatively, the at least one vaporizer condition includes monitoring the volume of liquid anesthetic agent in the sump to determine when the volume stops changing. Additionally, at 214, a timer starts to begin timing the length of time that the bottle is held in the filling position.

Next, at 212, it is determined whether or not at least one vaporizer condition has been met. If at least one vaporizer condition has been met, then the bottle is released from the filling position at 218. If at least one vaporizer condition has not been met, then it is further determined whether or not the timer has timed out by achieving a predetermined maximum length of time that the bottle should be held in the filling position. If the timer has timed out, then the bottle is also released from the filling position at 218. If the timer has not yet timed out, then the method returns to continue monitoring both the length of time that the bottle has been held in the filling position at 214 as well as the monitoring at least one vaporizer condition at 210.

Both of these types of monitoring are performed until at least one vaporizer condition is met at 212 or the timer times out at 216. Upon achieving one of these two conditions, the bottle is released from the filling position at 218.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

We claim:

1. A vaporizer filling system comprising:
an anesthetic agent source filled with liquid anesthetic agent;
a sump configured to receive liquid anesthetic agent;
a filler assembly connected to the sump, the filler assembly configured to couple with the anesthetic agent source;
a valve disposed between the anesthetic agent source and the sump, the valve controlling fluid communication between the anesthetic agent source and the sump;
a retaining device that retains the valve in an open position;
a delay connected to the retaining device, the delay controls the operation of the retaining device to retain the valve in the open position until the delay detects a release condition, wherein the delay controls the retaining device to release the valve.

2. The system of claim 1 wherein the anesthetic agent source is a bottle and the bottle is coupled to the filler assembly when the filler assembly is in a first position and the bottle is in a generally upward-opening orientation, the filler assembly further being rotatable between the first position and a second position about a pivot point and rotation of the filler assembly from the first position to the second position moves the valve between a closed position and an open position and moves the bottle into a generally downward-opening orientation.

3. The system of claim 2 wherein the valve is a bottle valve coupled to the bottle and disposed between the bottle and the filler assembly.

4. The system of claim 1 wherein the valve is a sump valve disposed between the filler assembly and the sump; and
wherein the anesthetic agent source is a bottle and movement of the filler assembly from a first position to a second position opens the sump valve and pours the liquid anesthetic agent from the bottle into the sump.

5. The system of claim 4, further comprising:
a bottle valve between the bottle and the filler assembly, wherein the movement of the filler assembly from the first position to the second position opens the bottle valve.

6. The system of claim 1 wherein the delay is a mechanical timer.

7. The system of claim 1 further comprising:
a sensor in association with the sump, the sensor measuring a condition of the sump; and
wherein the delay is an electronic controller, the electronic controller being coupled to the sensor, the electronic controller receiving the measured condition of the sump and the electronic controller operates the retaining device based upon the measured condition of the sump.

8. The vaporizer filling system of claim 7, wherein the measured condition of the sump is a volume of anesthetic agent in the sump, and the electronic controller operates the retaining device upon detecting a predetermined volume as a release condition.

9. The vaporizer filling system of claim 8, wherein the electronic controller includes a plurality of release conditions, and the electronic controller operates the retaining device upon detecting at least one of the plurality of release conditions.

10. The vaporizer filling system of claim 9, wherein the plurality of release conditions includes a measured length of time that the retaining device retains the filling assembly.

11. A method of filling a vaporizer comprising a filler assembly and a sump with a bottle of liquid anesthetic agent, a valve being disposed between the bottle of liquid anesthetic agent and the sump, the method comprising:
engaging the filler assembly with the bottle when the filler assembly is in a first position;
moving the bottle and the filler assembly from the first position to a second position to operate the valve to open fluid communication between the bottle and the sump;
locking the bottle and the filler assembly in the second position with a retaining device;
operating a controller to maintain the bottle and the filler assembly locked in the second position with the retaining device;
releasing retaining device locking the bottle and the filler assembly in the second position;
returning the bottle and the filler assembly to the first position.

12. The method of claim 11, wherein the bottle is engaged with the filler assembly such that the bottle moves in unison with the filler assembly; and further comprising the step of:
disengaging the bottle from the filler assembly once the filler assembly has returned to the first position.

13. The method of claim 11, wherein operating the controller further comprises the controller monitoring at least one release condition, the controller releasing the bottle and filler assembly from the retaining device upon sensing a release condition.

14. The method of claim 11, wherein the vaporizer comprises at least one sensor associated with the sump, and further comprising:
measuring, with the sensor, a condition of the sump; and
providing the measured condition of the sump to the controller;
wherein the at least one release condition includes a predetermined condition of the sump, and the controller maintains the bottle and filler assembly locked in the second position with the retaining device until the sensor measures the predetermined condition of the sump.

15. The method of claim 14, wherein the sensor measures the volume of anesthetic agent in the sump and the predetermined condition of the sump includes a volume of anesthetic agent in the sump.

16. The method of claim 15, wherein the at least one release condition further includes a predetermined length of time that the bottle and the filler assembly are locked in the second position and the controller further controls the retaining device to release the bottle and the filler assembly after the predetermined length of time has elapsed.

17. An anesthetic agent vaporizer, comprising:
a sump configured to retain liquid anesthetic agent;
a filler assembly in fluid communication with the sump, the filler assembly being configured for engagement with an anesthetic agent source, the filler assembly being further movable between a first position and a second position;
a valve disposed in the filler assembly, the valve regulates the fluid communication through the filler assembly into the sump wherein the valve is closed when the filler assembly is in the first position and the valve is open when the filler assembly is in the second position;
a retaining device that selectively engages the filler assembly to retain the filler assembly in the second position; and
a delay connected to the retaining device to control the operation of the retaining device to retain the filler assembly in the second position until the delay controls the retaining device to release the filler assembly to return to the first position.

18. The anesthetic agent vaporizer of claim 17 wherein the anesthetic agent source is a bottle of liquid anesthetic agent.

19. The anesthetic agent vaporizer of claim 18 wherein the delay is an electronic controller that monitors at least one release condition while the retaining device is operated to retain the filler assembly in the second position and the electronic controller operates the retaining device to release the filler assembly when the electronic controller determines that the at least one release condition has been met.

20. The anesthetic agent vaporizer of claim 19, further comprising a volume sensor associated with the sump, the volume sensor measuring a volume of the liquid anesthetic agent in the sump, wherein the at least one release condition comprises a predetermined volume of the liquid anesthetic agent in the sump, and the electronic controller operates the retaining device to release the filler assembly when the measured volume matches the predetermined volume of the at least one release condition.

\* \* \* \* \*